United States Patent

Ankner et al.

[11] Patent Number: 5,166,413
[45] Date of Patent: Nov. 24, 1992

[54] PROCESS FOR PREPARATION OF BRANCHED 1,3-GLYCOLS AND THEIR MONOESTERS

[75] Inventors: Kjell Ankner, Mölnlycke; Pia Carlsson, Bromma; Alfred Hopfinger, Bandhagen; Håkan Rahkola, Stenungsund; Kjell Sjöberg, Stocksund; Monica Söderlund, Stockholm, all of Sweden

[73] Assignee: Neste Oxo Aktiebolag, Sweden

[21] Appl. No.: 814,055

[22] Filed: Dec. 26, 1991

Related U.S. Application Data

[63] Continuation of Ser. No. 431,462, Nov. 2, 1989, abandoned.

[30] Foreign Application Priority Data

Nov. 2, 1988 [SE] Sweden .................. 8803978

[51] Int. Cl.$^5$ .............................. C07C 67/00
[52] U.S. Cl. ........................ 560/238; 568/252
[58] Field of Search ................. 560/238; 568/852

[56] References Cited

U.S. PATENT DOCUMENTS

| | | | |
|---|---|---|---|
| 3,091,632 | 5/1963 | Hagemeyer et al. | 260/476 |
| 3,291,821 | 12/1966 | Perry et al. | 260/494 |
| 3,703,541 | 11/1972 | Takasu et al. | 260/494 |
| 3,718,689 | 2/1973 | McCain et al. | 260/494 |
| 3,816,533 | 6/1974 | Brandstrom et al. | 564/291 |
| 4,225,726 | 9/1980 | Morris et al. | 560/238 |
| 4,273,934 | 6/1981 | Merger et al. | 560/238 |
| 4,883,906 | 11/1989 | Argyropoulos et al. | 560/238 |

FOREIGN PATENT DOCUMENTS

| | | |
|---|---|---|
| 2280518 | 11/1979 | Fed. Rep. of Germany . |
| 3024496 | 2/1982 | Fed. Rep. of Germany . |
| 3403696 | 8/1985 | Fed. Rep. of Germany . |
| 3447029 | 6/1986 | Fed. Rep. of Germany . |

OTHER PUBLICATIONS

Chemical Abstracts 90:103440f (1979).

*Primary Examiner*—Arthur C. Prescott
*Attorney, Agent, or Firm*—Brumbaugh, Graves, Donohue & Raymond

[57] ABSTRACT

The present invention relates to a process for the preparation of diols of the general formula (I)

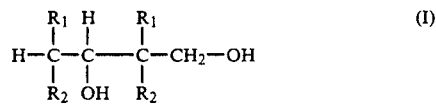

and monoesters thereof of the general formula (II)

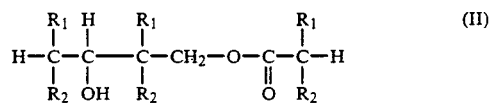

and the general formula (III)

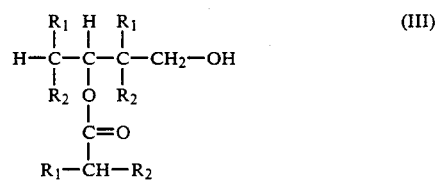

wherein $R_1$ and $R_2$ are the same of different groups and each denotes a lower alkyl group having 1 to 4 carbon atoms, preferably a methyl group. The process of this invention comprises condensing in a multi-phase reaction environment an aldehyde containing a hydrogen atom in the alpha position and having the general formula (IV)

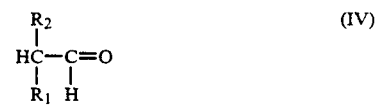

wherein $R_1$ and $R_2$ having the meaning given above, in the presence of a catalytic system consisting of a phase transferring catalyst and an alkaline substance.

11 Claims, No Drawings

PROCESS FOR PREPARATION OF BRANCHED 1,3-GLYCOLS AND THEIR MONOESTERS

This application is a continuation of application Ser. No. 07/431,462, filed on Nov. 2, 1989 now abandoned.

BACKGROUND OF THE INVENTION

The present invention relates to a process for the preparation of branched 1,3-glycols and their monoesters by means of a catalytic condensation reaction of aldehydes comprising a hydrogen atom in the alpha position.

The summary reaction can be described using the following formulae:

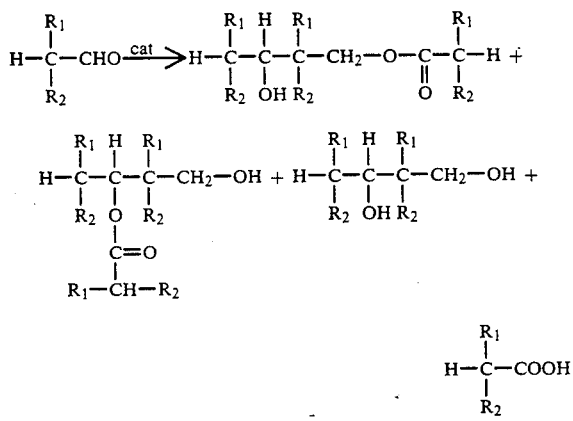

wherein $R_1$ and $R_2$ are the same or different groups, each being lower alkyl groups having 1 to 4 carbon atoms, preferably methyl groups. It is also probable that some amounts of 1,3-glycols are formed directly by means of an aldolization of the starting aldehyde by the following reaction according to Canizarro:

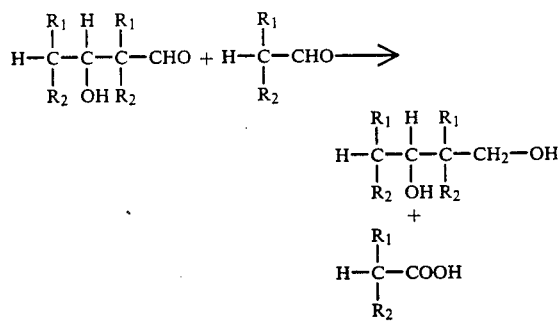

The above-described reactions have been known for about 50 years, and are described, for example, in German Patent No. DE-C-646,482. However, different technical problems in large scale production have raised and required improvements. Thus, improvements related to the preparation process are still of importance today. Another factor which has stimulated interest in the problem is the growing field of use both of the glycol as such, and of its monoester. The industrially largest raw material among the aldehydes which have a hydrogen atom in the alpha position is the isobutyric aldehyde. It is formed in considerable quantities by the hydroformylation of propene, the so-called OXO-process, as a by-product to n-butyric aldehyde.

As condensation catalysts, alkaline compounds have hitherto exclusively been used. Such compounds are most often readily dissolved in water, such as sodium hydroxide, and potassium hydroxide. Hydroxides of metals belonging to group 2A of the periodic table also show a satisfying catalytic activity. As the water is only slightly soluble in the reaction medium and inorganic hydroxides are practically insoluble in the organic phase, the condensation reaction continues in a two-phase system, and, when using the hardly soluble hydroxides of the group 2A, in a three-phase system. Most recent patents describe different methods regarding optimization of the difficultly controlled condensation reaction, but each have different drawbacks. For example:

U.S. Pat. No. 3,718,689 sets forth demands for both the purity of the isobutyric aldehyde—less than 0.5% of water and less than 0.5% organic acids—and the necessity of powerful stirring in order to obtain a stable emulsion in a two-phase system of concentrated hydroxide-aldehyde. The reaction time is considerably long and a satisfying yield is obtained first after about 2 hours. Tables show that the reproducibility of the process is very low. Thus in accordance with Table II of the subject patent, experiments 4, 5, and 6 have been carried out at apparently identical conditions, but quite different yields of monoester were obtained (i.e. 61%, 45%, and 20%, respectively).

A similar description of an alkali catalyzed process is found in U.S. Pat. No. 3,291,821, whereby powerful stirring and intense circulation are said to be necessary. Although powerful stirring is present, the yield of the batchwise process is still low, (i.e. only about 13%).

According to German Patent No. DE-A1-3,024,496, a stream of aldehyde and a stream of NaOH solution are introduced in parallel in a batchwise reactor. In this way one controls the intense evolution of heat and avoids the very rapid start of the reaction. This is particularly important if the reactor is initially completely filled by the reactants. One serious drawback of this process is that it is impossible to use it as a continuous process. This drawback is pointed out in the specification of the subject patent.

In U.S. Pat. No. 3,703,541 the use of phenolic salts as reaction catalysts is described and, according to U.S. Pat. No. 3,091,632, sodium alkanoates are used. Both these types of catalysts increase to some extent yield and selectivity, but they have difficult requirements as to the purity of the raw material and particular requirements as to the absence of water in the reaction environment. Thus, the processes are unattractive from an industrial viewpoint.

German Patent DE-2,820,518 discloses a catalytic system consisting of alkali earth metal hydroxides and carboxylic acids and their salts, respectively. A serious drawback of this process is that one has to precipitate the alkali earth metal catalyst using gaseous carbon dioxide after the final reaction. A troublesome separation of the fine grained precipitate will then become necessary.

German Patent DE-3,403,696 discloses a two step process consisting of a condensation reaction followed by a hydrogenation of raw reaction mixture at 120° C. and a pressure of 100 bars. It is not probable that such a process can be competitive against other methods described above, which only use conventional reactors provided with stirrers and tube reactors, respectively.

According to German Patent DE-A1-3,447,029 one obtains a good contact between water and an organic phase by using a tube reactor containing filler bodies —something that is well known to those skilled in the art.

U.S. Pat. No. 4,225,726 discloses a condensation reaction where tin and tin oxide, respectively, are used as catalysts. The advantage is that these catalysts make it possible to carry out synthesis reactions where aldehydes containing both one and two hydrogen atoms in the alpha position are used as a raw material. The yield of the condensation product containing only one hydrogen atom in the alpha position, as in the present invention is, when using isobutyric aldehyde, only 20%.

SUMMARY OF THE INVENTION

This invention is directed to a process for the preparation of diols and their monoesters, more particularly, branched 1,3 glycols and their monoesters. The process comprises condensing in a multi-phase reaction environment an aldehyde having a hydrogen atom in the alpha position and having the general formula

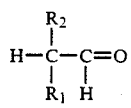

in the presence of a catalytic system which consists of a phase transfer catalyst and an alkaline substance to produce diols and monoesters thereof, the diols having the general formula

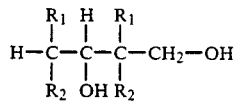

and the monoesters having the general formula

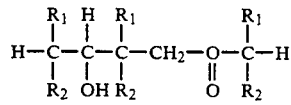

or

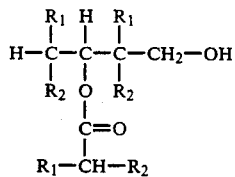

wherein $R_1$ and $R_2$ are each the same or different alkyl groups having 1–4 carbon atoms.

DESCRIPTION OF THE PREFERRED EMBODIMENTS

All the above-described difficulties can easily be reduced by using the present invention for the preparation of branched 1,3-diols of the general formula (I):

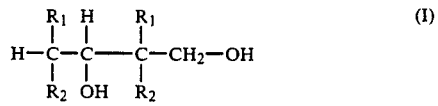

and monoesters thereof having the general formula (II):

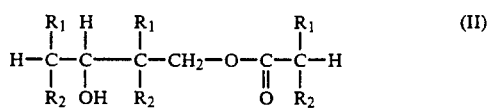

and the general formula (III)

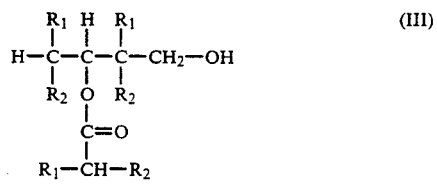

wherein $R_1$ and $R_2$ are the same or different groups, each being lower alkyl groups having 1 to 4 carbon atoms, preferably methyl. The process of this invention comprises condensing in a multi-phase reaction environment an aldehyde having a hydrogen atom in the alpha position, the aldehyde being of the formula (IV)

wherein $R_1$ and $R_2$ have the meaning given above, the condensation taking place in the presence of a catalytic system consisting of a phase transferring catalyst and an alkaline substance.

The invention is based on the use of a catalytic system consisting of a phase transferring catalyst in the presence of an alkali. This gives a number of important technical advantages:

(a) the reaction proceeds with a high speed;
(b) one obtains a high yield of reaction products;
(c) there is formed only small amounts of by-products;
(d) the process can be controlled either to the formation of diol or monoester as main product or to the formation of an arbitrary mixture of these two products;
(e) the catalyst can be recirculated;
(f) moderate stirring of the reaction mixture is sufficient; and
(g) the synthesis can be carried out either batchwise or continuously.

The phase transferring catalyst facilitates transport of hydroxy ions from the aqueous phase to the organic phase or to the phase border. As catalysts, quaternary ammonium-, phosphonium-, and arsonium salts are most often used, as well as cyclic and straight aliphatic polyethers as well as certain chelate forming agents.

When an onium salt is being introduced into an alkaline aqueous solution the following ion exchange can take place:

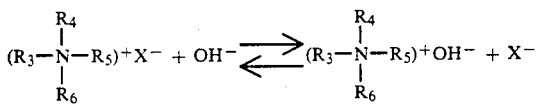

wherein $R_3$, $R_4$, $R_5$ and $R_6$ are hydrocarbon radicals and $X^-$ is an anion.

The ion pair formed is extracted from the aqueous phase to the organic phase or border surface where the $OH^-$ group catalyzes the condensation reaction. Phase transferring catalysts of polyether structure behave somewhat differently in that they form a chelate compound with a metal cation, while the hydroxy group lies outside the chelate structure. The system polyether-metal cation-hydroxy ion formed is easily extracted to the organic phase.

There are three factors which decide the extractability of the $OH^-$ group to the organic phase or the concentration at the phase border. Primarily: the concentration of the hydroxy anion in the aqueous phase —the more concentrated the aqueous solution is the greater the disposition of the ion pair to be transferred to the organic phase. Secondly: the hydrophobicity of the phase transfer catalyst—the more carbon atoms the onium salt contains, the higher will the extraction coefficient become. The cooperation between these parameters introduces great optimizing possibilities with regard to reaction speed, selectivity, and design of the reactor.

Among different types of formers of hydroxy ions, hydroxides and oxides belonging to groups IA and IIA of the periodic table are most favorable, i.e., sodium hydroxide, potassium hydroxide, lithium hydroxide, calcium hydroxide, magnesium hydroxide, and barium hydroxide. Sodium hydroxide and potassium hydroxide are preferably used in technical industrial processes. The concentration of hydroxy ions in an aqueous phase may vary within a broad range.

Even a 5% solution can give a good yield of the end product if the catalyst is hydrophobic enough. On the other hand one may use a 50% solution of alkaline substance whereby the reaction proceeds very rapidly but the end product may become yellow or brown colored. The optimal concentration is in the range of 15 to 40%. The amount of hydroxide used also has an impact as to which end product shall be obtained. The monoesters can suitably be produced using catalyst up to molar amounts of hydroxy ions, while the diol demands at least molar amounts of hydroxy ions to be completely formed. In the presence of a phase transferring catalyst, the hydrolysis of the monoester formed proceeds very quickly and quantitatively.

Extraction of hydroxy ion from the aqueous phase to different types of organic phase using transfer catalysts has been investigated and is known to those skilled in the art, as exemplified by Dehmlov, E. V., Dehmlov, S. S.—Phase Transfer Catalysis—II ed. —Verlag Chemie, p. 33-41; Landini, D., Maja, A., Montanari, F., Israel Jour. of Chemistry, 26, (1985), p. 263-269; Gokel, G. W., Goli, D. M., Schulz, R. A., J. Org. Chem., 48. (1983), p. 2837-42: and Dehmlov, E. V., Slopianka, M., Heider, J., Tetrahedron Lett. (1977), p. 2361. The general conclusion is that the more hydrophobic the onium catalyst is the more effective it will transport the $OH^-$ ion in the organic phase. The efficiency of the polyethers are dependent on the chemical structure of the organic phase.

The experiments carried out and shown below show that extraction of hydroxy ion from aqueous phase to a mixture of isobutanal and its reaction products takes place in a satisfying way using onium catalysts containing at least 8 carbon atoms in their structure. The following cation structures have been shown to be particularly suitable: trioctyl ammonium; lauryl benzylammonium; methyl triheptylammonium; tetrabutylammonium; tetraisopropylammonium; tetraethylammonium; tetrapentylammonium; tetrahexylammonium; cetyltributylphosphonium; ethyl tributyl phosphonium; tetrabutylphosphonium; and benzyl triethylphosphonium. As an anion to these quaternary cation structures, sulphate, bromide, chloride acetate and other anions which are not acidic and/or not too lipophilic may be used. Very interesting results were obtained using straight chained polyethers. The polyglycolether having a mean molecular weight of between 200 and 400 turned out to be a very efficient phase transfer catalyst. Higher polymers of ethylene oxide are catalytically active, as well, but increasing viscosity of the reaction mixture makes their use more difficult.

The amount of the phase transfer catalyst can be varied within rather wide limits, between 0.02 to 10 mol % calculated in relation to the amount of starting aldehyde. The optimal range is between 0.25 to 4 mol %. After finalized reaction, the catalyst is separated depending on its chemical structure in different quantitative relationships in the aqueous and organic layers. It can also be separated from the two phases and recirculated. Separation from the aqueous phase takes place using an extraction agent, where particularly lower esters and chlorinated hydrocarbons are suitable. Separation from the organic phase is most conveniently done by means of distillation where one recovers the catalyst as a distillation residue. If the diol is being purified by recrystallization, the catalyst will end up in the mother liquid and can be easily separated as a residue at the regeneration of the solvent. The organic layer can most often be freed from catalyst by extraction using a weak alkaline aqueous solution.

The reaction temperature can vary within a range of between 40° and 150° C. In order to reach the upper limit it is necessary to use a high overpressure. This is not profitable in practice as the reaction proceeds at a satisfying rate at 60° to 90° C. This means that the working pressure of the process can be between 0.8 to 4 atmospheres absolute pressure.

The catalytic synthesis method described facilitates the use of different types of reactors. One can thus carry out the reaction both batchwise and continuously. Short reaction times—particularly at the synthesis of monoesters—facilitates the use of tube reactors, as no particularly intensive stirring is required. Thus, through-flowing tank reactors either in the form of single apparatuses or in the form of batteries of apparatuses of two or more units may be used. An interesting solution of a tube reactor design is a combination of tube reactor and tank reactor. If one wants to produce mainly monoesters, then the tube reactor is used only where the residence time seldom exceeds 10 min. On the other hand, if one should want to have the diol only or mainly, then the stream of reactants from the tube reactor is introduced into a larger through-flow tank reactor, where a complete hydrolysis takes place. The process is most easily finished by stopping the stirring. Two separate phases are then quite rapidly formed and the reaction stops when the OH⁻ ions present in the organic layer have been used. A similar result is obtained by introducing an acid in the reaction environment, which neutralizes the free alkaline compounds, and by cooling down the reaction mixture, respectively.

If the process proceeds batchwise then it is convenient to first introduce the catalytic systems, i.e. water, hydroxide/oxide, and catalyst into the reactor, heat this mixture to about 60° C., and then introduce the aldehyde. In the presence of the phase transfer catalyst the reaction starts without any introductory period. The dose rate is determined in practice by the efficiency of a reflux cooler arranged in the system. After finished dosage, the reaction mixture is stirred for some time. If it is a monoester which is produced and this is the reaction product desired, the stirring time should not exceed a few minutes and a small amount of hydroxide ions should be used. If it is the diol which is the product desired, the reaction depends on the molar amount of hydroxide ions. The stirring time may vary between 5 to 90 min. One may also add the alkaline solution and the aldehyde in parallel, but then, one should have already introduced the total amount of phase transfer catalyst, dissolved or suspended in water into the reactor. One might also control the process course by using solvents, in particular aromatic hydrocarbons and higher alcohols. In the presence of solvents the reaction mixture will boil less intensively and the color of the products will improve to some extent as well. The separation of the catalyst may also be made easier.

As have been disclosed in German Patent Nos. DE-A1-3,102,826 and DE-A1-3,024,496, it is advantageous to free the reaction mixture from the readily boiling products and to decompose the trimeric structures of the starting aldehyde by distillation in the presence of water, which is introduced after finished synthesis. In order to achieve a complete decomposition, it may be necessary to use a temperature of up to 150° C. and 10 bar super pressure, as in German Patent No. DE-A1-3,024,496, p. 5. The same result can be obtained at considerably milder conditions if the distillation of the system of reaction mixture and water proceeds in the presence of phase transfer catalyst. Then it is enough using atmospheric pressure, and a slight overpressure, respectively, which is created under the influence of the flowing resistance. The temperature in the distillation head will thereby not exceed 80° C. and the decomposition of the polymeric structures continues very quickly. Most often the amount of catalyst present in the organic phase is enough after finished synthesis step. In certain cases it can, however, turn out necessary, to add a minor amount of fresh catalyst. There are two ways to add water to the system: either in one step to the distillation vessel or it is added continuously during the course of the distillation into the head of the column or directly into the vessel. The adding of hot water is preferred prior to adding cold water.

EXAMPLE 1

In a flask provided with a reflux cooler, a stirrer, a bottom valve, a dosing funnel, and a thermometer, 50 g of o-xylene, 80 g of 25% NaOH aqueous solution, and 2.5 g of trioctylmethyl ammoniumchloride were added. The mixture was heated, while stirring, to 60° C. At this temperature the addition of 144 g of isobutanal was started. The time for addition was 13 min. and the temperature increased under moderate boiling to 77° C. Then the temperature fell slowly to 60° C. and was kept at this temperature to the end of the test. Under the course of the reaction samples were taken for chromatographic analysis, shortly after completion of the addition, and 5, 10, 30, 60 and 180 min. after completion of the addition. Analytical data gave the following information: (a) summary yield of ester and diol were not changed after stirring for 5 to 10 min., (b) after this time hydrolysis of only the monoester took place, and it was finished after a maximum of 30 min., (c) in the reaction mixture only minimal amounts of by-products were found.

After finished reaction the phases were separated. The organic phase was evaporated in vacuo at 60° C. The residue consisted of water clear liquid containing white crystals. It consisted of the monoester (2 isomers) and the diol in a molar ratio of 1.3:1. Summary yield of these products was 47%. The aqueous phase did not contain any free sodium hydroxide. After treatment with conc. hydrochloric acid an organic layer was formed consisting of isobutyric acid and a small amount of neutral compounds. Yield of crude isobutyric acid was 41 g.

EXAMPLE 2

In order to determine the influence of the phase transfer catalyst the experiment according to Ex. 1 was repeated but without the use of any trioctylmethyl ammoniumchloride. During the addition of isobutanal no reaction took place. After 25 min. of stirring at 60° C. the reaction was suddenly started and the temperature rose to 76° C. The stirring continued and samples were taken out in accordance with Ex. 1. The reaction was practically finished after 10 min., but the summary yield of the reaction product was only 20%, of which 8% was diol.

EXAMPLE 3

The experiment according to Ex. 1 was repeated with the difference that methyl trioctylammoniumchloride (Aliquat 336, Henkel, DE) was used as phase transfer catalyst. The results obtained corresponded completely with those obtained in Ex. 1.

EXAMPLE 4

The experiment according to Ex. 1 was repeated with the difference that tetrabutylammoniumsulphate was used as phase transfer catalyst. The results obtained corresponded completely with those obtained in Ex. 1.

EXAMPLE 5

The object of this experiment was to obtain a major part as monoester. The experiment in accordance with Ex. 1 was repeated but after an additional time of 13 min. the stirring took place during 90 seconds only, whereupon the stirring was stopped and the two phases were separated. The organic phase was distilled. The main product consisted of 12.3 mol-% of diol and 87.7 mol-% of monoester. The yield of the main product was 55.3%.

EXAMPLE 6

In a flask provided with a bottom valve, reflux cooler, stirrer, additional funnel, and a thermometer there was introduced 40 g of a 20% NaOH solution and 16 g of polyethyleneglycol having a mean molecular weight of 400. The contents of the flask were heated while stirring to 60° C. 144 g of isobutanal were added during 4.5 min. While adding, the temperature was raised to 77° C. and the reaction mixture boiled. After finishing the addition the temperature was increased to 80° C. and was kept at this level for 2 hrs. Samples for analysis were taken out 1, 3, 8, 15, 30, and 60 min. after finished addition. The analysis showed that the reaction was completed after 8 min. After 2 hrs. stirring the phases were separated and 64.6 g aqueous phase and 123 g of organic phase were obtained. Loss as well as material for analysis were 12.4 g. The aqueous phase was acidified with an excess of hydrochloric acid and 30.7 g of water insoluble layer consisting of isobutyric acid mixed with small amounts of neutral substances was thereby obtained. The organic phase was distilled in the presence of water and catalyst. The residue consisted of a water clear liquid (94.2 g) consisting of the monoester, and diol, and a small amount of catalyst. By distillation in vacuo, 81 g of the main product were obtained consisting of the monoester and diol in a molar ratio of 5:1. 10 g of the residue consisted of recovered catalyst mixed with the reaction products.

Distillation of the acidic phase separated from the water phase gave 20 g of a distillate and 10 g of a residue.

The distillation residues containing the catalyst were mixed together, 5 g of fresh catalyst were added, and the synthesis was repeated. The reaction course was the same as during the first, above-described run.

EXAMPLE 7

The apparatus of a continuous process consisted of two dosing pumps of which one added isobutanal containing 2.8% by weight of polyethylene glycol ($M_w$ 400) and the other added 15% NaOH solution. The amount of NaOH as 100% was equal to 3.4% by weight of the amount of isobutanal. The two solutions were pumped through heated glass tubes where they were heated to 55° C. and were then introduced into a stirring reactor consisting of a 100 ml flask provided with an inlet and an outlet tube, a thermometer, a reflux cooler, and a stirrer with its shaft through the reflux cooler. The average residence time of the reaction mixture in the reactor was 1.9 min. The temperature of the flask was 70° C. From the reactor, the reaction mixture flowed to a separator where the entering phases were separated. A gas chromatography analysis of the organic phase showed that the yield of the monoester (2 isomers) was 20.7% and trimethylpentadiol 0.2%.

EXAMPLE 8

The same apparatus for continuous production as used in Ex. 7 was used with the difference that the shape of the reactor was somewhat different. Thus the reactor consisted of a glass tube having a diameter of 2.2 cm and a height of 18 cm. It was provided with an inlet and an outlet tube, a thermometer, an efficient reflux cooler, and a tube led through the reflux cooler, the tube reaching the bottom of the reactor. The inner diameter of the latter tube was 2 mm. A stream of nitrogen gas was continuously fed through this tube and in this way a stirring of the reaction mixture was obtained. The pumps added isobutanal containing 1% by weight of polyethyleneglycol ($M_w$ 400) and a 25% solution of NaOH. The amount of NaOH, as 100%, was equal to 2.5% by weight of the amount of isobutanal added. The reactants were added to the reactor without being previously preheated. The residence time of the reaction mixture in the reactor was 42 seconds. The reaction was initiated by heating the reactor to about 60° C. When the reaction started the heating bath was removed. The temperature of the reactor was stabilized at 69° to 70° C. The phases were separated in the separator. When the process had become stable samples were taken out for analysis. A gas chromatographic analysis showed that the yield of the monoester (2 isomers) was 30% calculated on the amount of isobutanal added. The corresponding yield of trimethyl pentadiol was 1%.

As a comparison it can be pointed out that when using a back-mixing process without phase transfer catalyst using NaOH solution only as in U.S. Pat. No. 3,718,698, Ex. 2, the residence time in the reactor was 1 hr., i.e. 30 to 90 times longer than in a process according to the present invention.

We claim:

1. A process for the preparation of diols of the formula

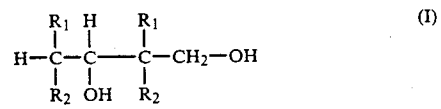

and monoesters thereof of the formula

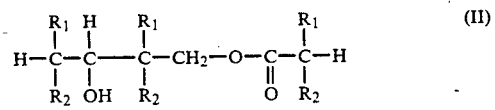

and

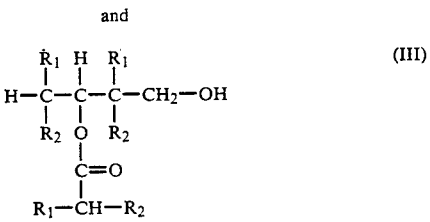

the process comprising condensing in a multi-phase reaction environment an aldehyde having a hydrogen atom in the alpha position in the presence of a catalytic system consisting of a phase transfer catalyst and an alkaline substance, the aldehyde having the formula:

wherein $R_1$ and $R_2$ are each alkyl groups having 1–4 carbon atoms, and a distillation of light reaction products and decomposition of polymeric structures formed by the aldehyde present take place in the presence of the phase transfer catalyst after finalized reaction.

2. A process according to claim 1, in which $R_1$ and $R_2$ are methyl groups.

3. A process according to claim 1, in which the phase transfer catalyst is selected from the group consisting of quaternary ammonium compounds, quaternary phosphonium compounds, quaternary arsonium compounds, polyalkylene glycolethers, and cyclic polyesters.

4. A process according to claim 1, in which the aldehyde is isobutanal.

5. A process according to claim 1, in which the molar ratio between base and aldehyde for the production of monoesters according to formula (II) and formula (III) is 0.2–1.1:1.

6. A process according to claim 1, in which the molar ratio between base and aldehyde for the production of diols according to formula (I) is 0.5–2.0:1.

7. A process according to claim 1, in which the reaction is carried out at a temperature in the range of 40°–150° C.

8. A process according to claim 7, in which the reaction is carried out at a temperature in the range of 60°–90° C.

9. A process according to any one of claims 1–8, in which the reaction is stopped by implementing one or more steps selected from the group consisting of stopping the ongoing stirring and separation of the phases present, neutralizing the alkaline compound present by treatment with an acid, and cooling the reaction mixture.

10. A process according to claim 1, in which the process is carried out batchwise.

11. A process according to claim 1, in which the process is carried out continuously.

* * * * *

UNITED STATES PATENT AND TRADEMARK OFFICE
CERTIFICATE OF CORRECTION

PATENT NO. : 5,166,413
DATED : November 24, 1992
INVENTOR(S) : Ankner et al.

It is certified that error appears in the above-identified patent and that said Letters Patent is hereby corrected as shown below:

Abstract, line 8: "same of" should read --same or--;

Abstract, line 3: "having" should read --have--.

Signed and Sealed this

Ninth Day of November, 1993

Attest:

BRUCE LEHMAN

Attesting Officer

Commissioner of Patents and Trademarks